United States Patent
Terry

(10) Patent No.: US 11,468,726 B2
(45) Date of Patent: Oct. 11, 2022

(54) SAFETY SYSTEM EMBODYING TOOLS TO ASSESS, MONITOR AND DOCUMENT TRAFFIC IN A PERIOPERATIVE SETTING

(71) Applicant: Lisa Carroll Terry, Fort Worth, TX (US)

(72) Inventor: Lisa Carroll Terry, Fort Worth, TX (US)

( * ) Notice: Subject to any disclaimer, the term of this patent is extended or adjusted under 35 U.S.C. 154(b) by 356 days.

(21) Appl. No.: 16/811,821

(22) Filed: Mar. 6, 2020

(65) Prior Publication Data
US 2021/0125444 A1 Apr. 29, 2021

Related U.S. Application Data

(60) Provisional application No. 62/926,121, filed on Oct. 25, 2019.

(51) Int. Cl.
| | |
|---|---|
| *G07C 9/37* | (2020.01) |
| *G06Q 50/26* | (2012.01) |
| *G06K 7/14* | (2006.01) |
| *G07C 9/00* | (2020.01) |
| *G07C 9/28* | (2020.01) |
| *G06K 7/10* | (2006.01) |
| *A61B 5/1171* | (2016.01) |
| *A61B 5/1172* | (2016.01) |
| *G16H 10/60* | (2018.01) |
| *G10L 17/00* | (2013.01) |
| *G06V 40/16* | (2022.01) |
| *G06V 40/18* | (2022.01) |
| *G06V 40/12* | (2022.01) |

(52) U.S. Cl.
CPC .............. *G07C 9/37* (2020.01); *A61B 5/1171* (2016.02); *A61B 5/1172* (2013.01); *A61B 5/1176* (2013.01); *G06K 7/10366* (2013.01); *G06K 7/1413* (2013.01); *G06K 7/1417* (2013.01); *G06Q 50/265* (2013.01); *G07C 9/00904* (2013.01); *G07C 9/28* (2020.01); *G10L 17/00* (2013.01); *G16H 10/60* (2018.01); *G06V 40/1365* (2022.01); *G06V 40/172* (2022.01); *G06V 40/197* (2022.01)

(58) Field of Classification Search
CPC ..................................................... G07C 9/37
USPC ........................................................ 705/3
See application file for complete search history.

(56) References Cited

U.S. PATENT DOCUMENTS

| | | | |
|---|---|---|---|
| 10,822,648 B1* | 11/2020 | Patel | C12Q 1/701 |
| 11,224,673 B1* | 1/2022 | Kellogg, Jr. | A61L 2/22 |
| 2015/0322696 A1* | 11/2015 | Dudley | E05B 65/06 |
| | | | 292/213 |
| 2019/0362837 A1* | 11/2019 | Guarino | G06Q 10/06311 |
| 2021/0115707 A1* | 4/2021 | Le | E05C 1/12 |
| 2021/0123267 A1* | 4/2021 | Kiang | E05B 47/0669 |
| 2021/0125444 A1* | 4/2021 | Terry | G06K 7/10366 |
| 2021/0287469 A1* | 9/2021 | Ryhorchuk | G06V 40/172 |
| 2021/0388641 A1* | 12/2021 | Ashcroft | E05B 13/106 |
| 2022/0014947 A1* | 1/2022 | Smith | H04W 28/0268 |
| 2022/0112743 A1* | 4/2022 | Hickman | E05B 59/00 |

* cited by examiner

*Primary Examiner* — Allyson N Trail
(74) *Attorney, Agent, or Firm* — Dunlap Bennett & Ludwig, PLLC

(57) ABSTRACT

A perioperative safety system embodying tools to assess, monitor and document traffic in the perioperative operating room setting to reduce risk of infection for a surgical patient by enforcing the reduction and elimination of unnecessary traffic in the operating room setting.

19 Claims, 14 Drawing Sheets

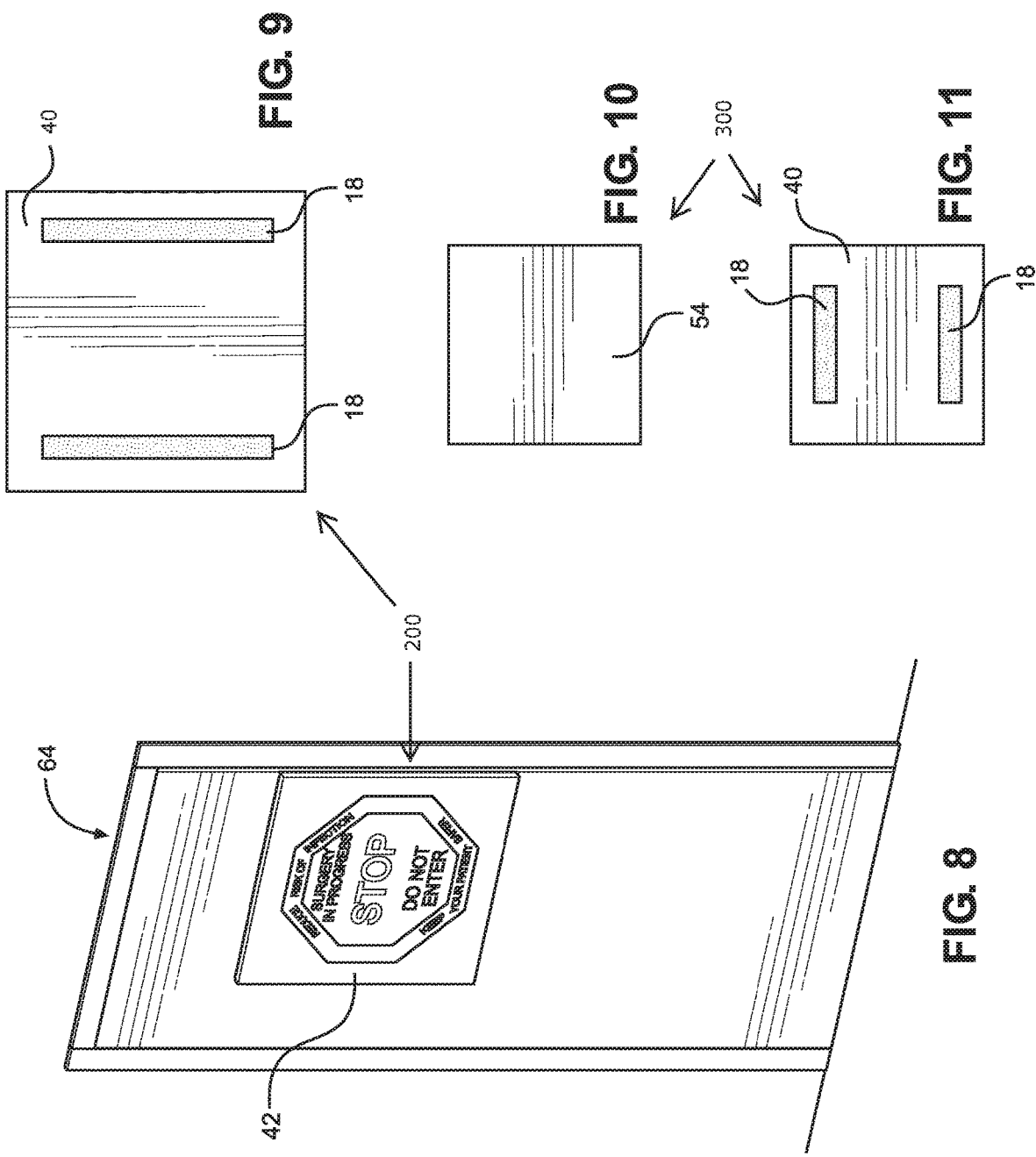

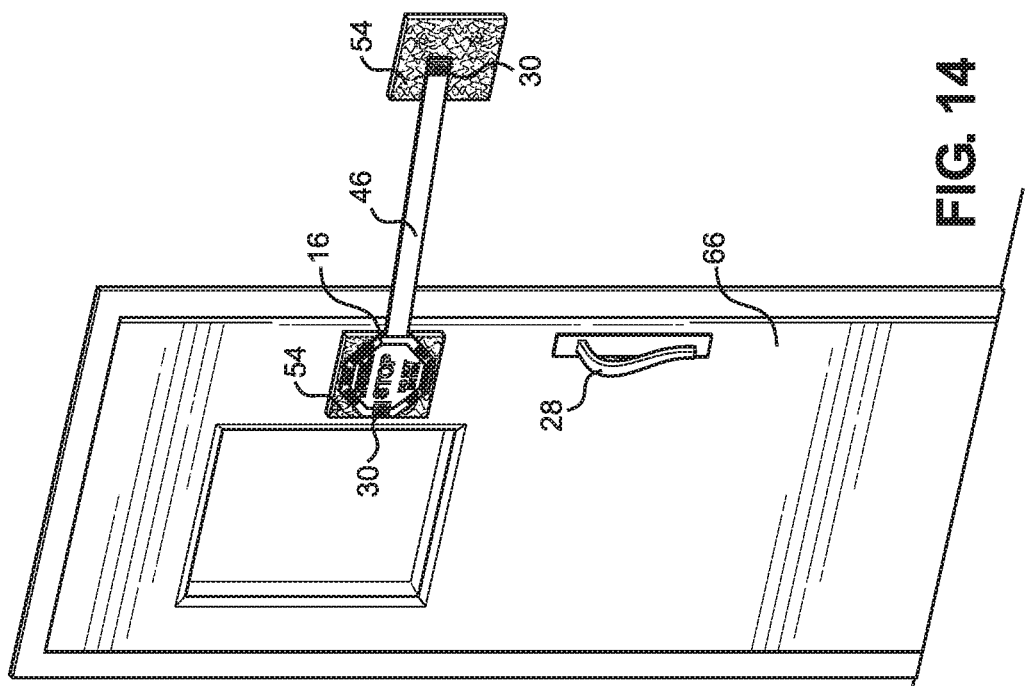
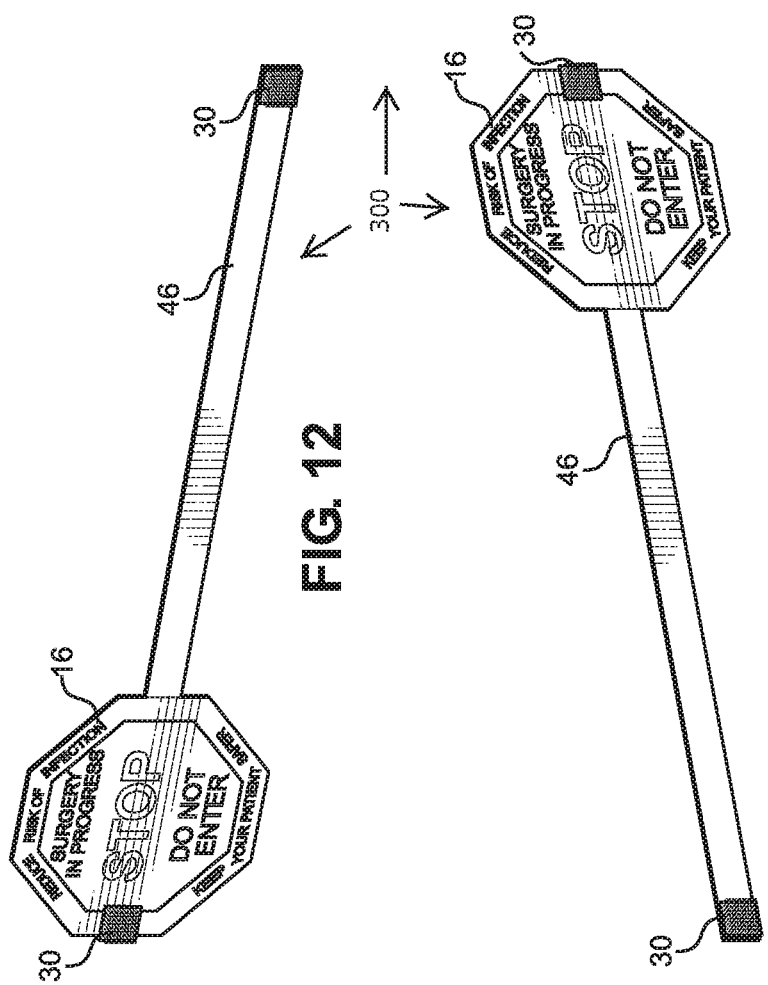

SAFETY SYSTEM EMBODYING TOOLS TO ASSESS, MONITOR AND DOCUMENT TRAFFIC IN A PERIOPERATIVE SETTING

CROSS-REFERENCE TO RELATED APPLICATION

This application claims the benefit of priority of U.S. provisional application No. 62/926,121, filed 25 Oct. 2019, the contents of which are herein incorporated by reference.

BACKGROUND OF THE INVENTION

The present invention relates to perioperative safety systems and, more particularly, a perioperative safety system embodying tools to assess, monitor and document traffic in the perioperative operating room setting to reduce risk of infection for a surgical patient by enforcing the reduction and/or elimination of unnecessary traffic in the operating room setting.

Operating room traffic is at a shockingly high rate. Such traffic exposes vulnerable patients, only prepared for a sterile surgical procedure, to bacteria and other airborne contaminates that can lead to infections and other complications. This threat of airborne and bacterial contamination is known, yet practices to prevent unwanted exposure to patients are not enforced and preventive measures to limit unnecessary intrusion reside solely on personnel in the sterile suite, which are not in place.

Currently, there are no manual, computerized or digital systems or devices in place to asses, monitor and document unnecessary intrusion of bacteria and other airborne contaminated through perioperative trespass of the hoped-for sterile perioperative suite. The Association of periOperative Registered Nurses (AORN) evidenced-based recommendations are to limit traffic patterns in the surgical suite to deliver safe patient care. Previous methods of monitoring and reporting have been dependent on unreliable human discretion, as well as surgeon request. Simply put, there are no systems in place that demand personnel remain aware and stay focused on minimizing unnecessary operating room traffic for the safety of the patient.

As can be seen, there is a need for tools to assess, monitor and document traffic in the perioperative setting to reduce the risk of infection for each surgical patient while reducing and/or eliminating unnecessary traffic in the operating room setting. The present invention demands awareness of perioperative personnel through monitoring and documentation reporting tools, thereby decreasing and possibly eliminating unnecessary operating room traffic, and so ultimately minimizing unnecessary bacteria and other airborne contaminants to contact a patient undergoing a sterile surgical procedure.

The mechanical devices embodied in the present invention alert outside personnel not to enter the sterile suite during sterile procedures, documents their entry into the area, and reports intrusions to supervisors and becomes a part of the patient's medical record.

As a result, the present invention demands strict reliable assessment, monitoring and documentation as well as provides a method of reporting. The system embodied in the present invention can be used to improve processes and provide a reliable record of all intrusions into the operating room suite while surgical procedures are being performed. The evidence resulting from the invention's results will provide distinctive properties noticeably different in the practice of employees, vendors, sales representatives, and the like within each hospital or medical facility.

Specifically, the results from the invention will demonstrate and provide factual results of traffic in the operating room setting. Having an assessment, monitoring and documentation system in place utilizing the present invention will hold previous and current recommendations in the forefront of current practices and will reduce and eliminate the need for unnecessary intrusions in the operating room while surgical procedures are being performed. Holding employees, vendors, sales representatives, stakeholders, and facilities accountable and responsible for following AORN guidelines to reduce the risk of infection is paramount for the safety of the patient.

SUMMARY OF THE INVENTION

In one aspect of the present invention, a perioperative safety system for eliminating unnecessary traffic in an operating room setting, includes the following: main doors for accessing and egressing the operating room setting; an outer perioperative safety device disposed adjacent an outer portion of the main doors, wherein accessing the operating room setting through said main doors requires engaging said outer perioperative safety device; and an inner perioperative safety device disposed adjacent an inner portion of the main doors, wherein accessing the operating room setting through said main doors requires moving said inner perioperative safety device, wherein the outer perioperative safety device is electrically connected to a computer, wherein the computer is electrically connected to a medical record of a patient undergoing a surgery in the operating room setting, and wherein engaging said outer perioperative safety device during said surgery is saved in the medical record, wherein the outer perioperative safety device is a touchscreen entry device, a facial recognition entry device, an eye-scan entry device, a voice biometric entry device, a palm-print-scan entry device, a contactless chip reader entry device, a barcode entry device, a QR-scan entry device, and/or a finger-print entry device.

In another aspect of the present invention the perioperative safety system provides an outer perioperative safety device is a generally planar body including the following: a center portion extending between a first and second warning structures; a pull tab extending from the first and second warning structures away from the center portion; the generally planar body foldable between an operable condition and a slidable condition dimensioned to slid through a gap between the main doors, wherein the operable condition mates the first and second warning structures; and a warning indicium provided along the first and second warning structures, wherein the warning indicium is visible when accessing the operating room setting through said main doors, wherein the warning indicium comprises verbiage that alerts personnel of the patient, wherein the planar body comprising a plurality of fold lines for so that the planar body is foldable, wherein the first and second warning structures each provide a flange that mates with the other flange in the operable condition, wherein the planar body comprises a centrally disposed pull tab opening, and wherein the two pull tabs extend through the pull tab opening when folding from the slidably condition to the operable condition; the pull tab opening providing two diametrically opposing pulse-shaped voids extending upward and downward, respectively, wherein a spaced between the distal tips of each pulse-shaped voids is dimensioned so that the two pull tabs extend therethrough, wherein the two pull tabs are disposed along the inner portion of the main doors, and wherein the first and second warning structures are disposed along the outer portion of the main doors in the operable condition.

In yet another aspect of the present invention the perioperative safety system provides the inner perioperative safety device having two connection points; a sign with a warning indicia; and a band, wherein the sign and each band removably attaches to one of the two connection points, respectively, so that the band extends across the gap of the main doors, wherein the one of the two connection points associated with the sign is at least twice as connected to the sign as the other of the two connection points is connected to the band.

These and other features, aspects and advantages of the present invention will become better understood with reference to the following drawings, description and claims.

BRIEF DESCRIPTION OF THE DRAWINGS

FIG. 8 is a perspective view of an exemplary embodiment of the second perioperative safety device 200 of the present invention shown in use along an exterior of sub sterile door of an operating room;

FIG. 9 is a back view of an exemplary embodiment of the second perioperative safety device 200 of the present invention;

FIG. 10 is a front view of an exemplary embodiment of the third perioperative safety device 300 of the present invention;

FIG. 11 is a back view of an exemplary embodiment of the third perioperative safety device 300 of the present invention;

FIG. 12 is a front view of an exemplary embodiment of the third perioperative band barrier safety device 300 of the present invention;

FIG. 13 is a back view of an exemplary embodiment of the third perioperative band barrier safety device 300 of the present invention;

FIG. 14 is a perspective view of an exemplary embodiment of the third perioperative safety device 300 of the present invention shown in use from an interior of an operating room;

FIG. 26 is an elevation view of an exemplary embodiment of a sticker of the present invention, wherein the sticker may be placed in patient medical records after a procedure is complete with information filled in;

DETAILED DESCRIPTION OF THE INVENTION

Figure 1:
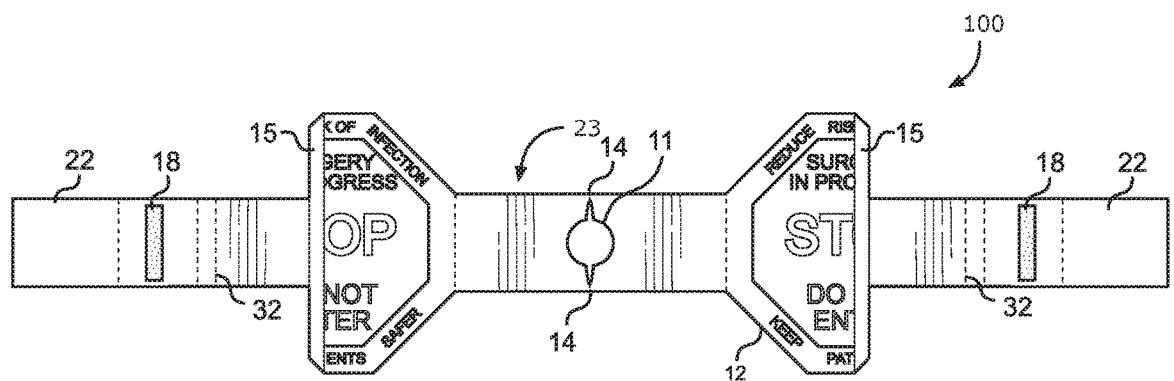
FIG. 1 is a front elevation view of an exemplary embodiment of a first perioperative safety device 100 of the present invention before assembled.
Figure 2:
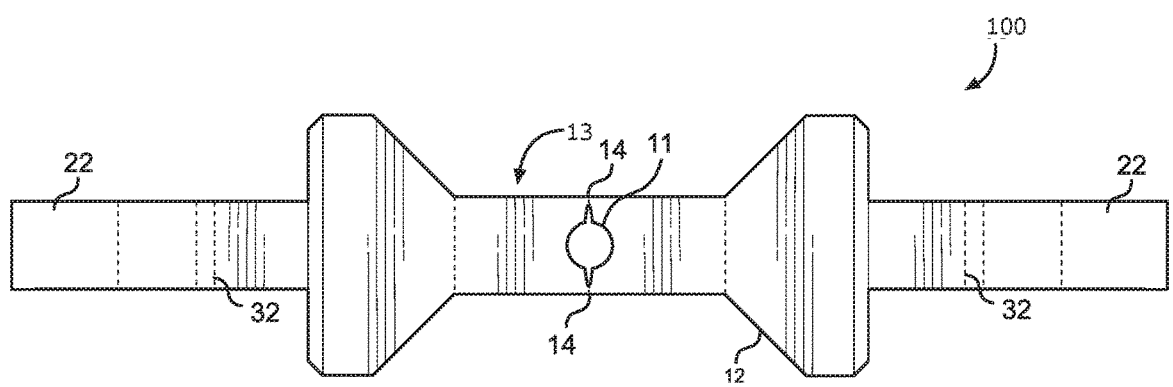
FIG. 2 is a rear elevation view of an exemplary embodiment of the first perioperative safety device 100 of the present invention before assembled.
Figure 3:
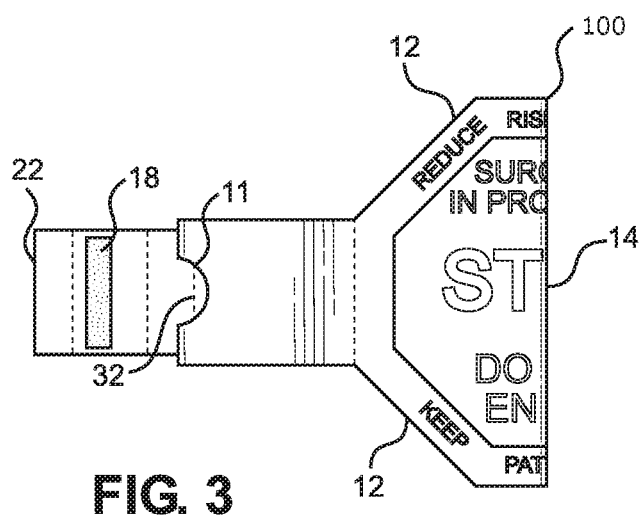
FIG. 3 is a side elevation view of an exemplary embodiment of assembled first perioperative safety device 100 of the present Invention.
Figure 4:
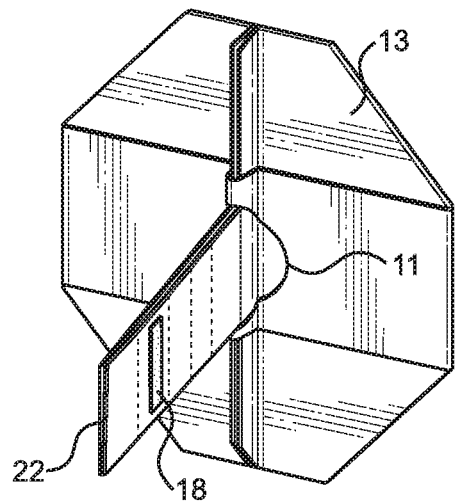
FIG. 4 is a back view of an exemplary embodiment assembled first perioperative safety device 100 of the present Invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Referring now to FIGS. 1 through 7, the perioperative safety system of the present invention provides a first perioperative safety device 100 adapted to fold between an operative condition and a slidable condition so as to pass through a gap 60 between the main doors 62 and to unfold into the operative condition when deployed on the other outward-facing side of said main doors 62.

A surgical theatre typically has at least two entry or exit points. The main doors 62 and the sub sterile door 64. The main doors 62 can also be defined as two distally-pivotably-connected operating doors, and also be known as the first set of closed doors or main entrance doors. The sub sterile door 64 may be known as the secondary access door, the second set or single door(s) of a second entry point.

The first perioperative safety device 100 may be made from approved disposable hospital approved NFPA Hospital Fire and Safety Code paper or equivalent. The first perioperative safety device 100 has opposing front and rear surfaces 23 and 13. The first perioperative safety device 100 provides a plurality of fold lines for folding between the operative and the slidable conditions.

The first perioperative safety device 100 extends between two opposing tabs 22. A pull tab opening 11 may be provide a midpoint between the two opposing tabs 22, wherein the pull tab opening 11 is dimensioned and adapted to slidably received both tabs 22 therethrough when folded into the operable condition. The pull tab opening 11 may be generally circular with two diametrically opposing pulse-shaped voids extending upward and downward, respectively. It is through the spaced between the distal tips of each pulse-shaped voids that the tabs 22 slide. Also, at said distal tips, a main fold line 14 may extends so as to enable the first perioperative safety device 100 to fold in half.

Figure 5:
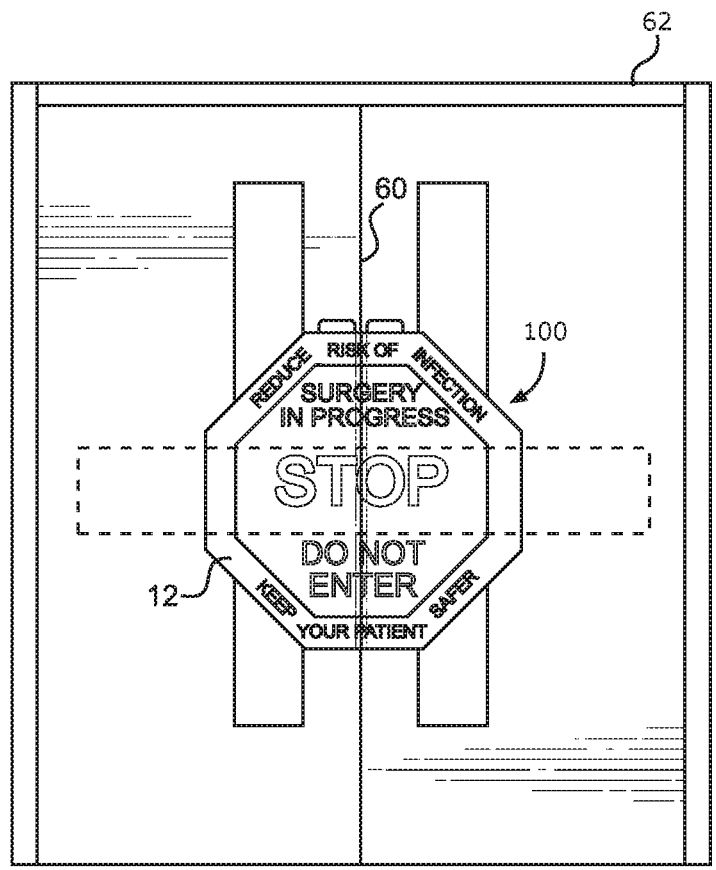
FIG. 5 is a perspective view of an exemplary embodiment of the first perioperative safety device 100 of the present invention shown in use.
Figure 7:
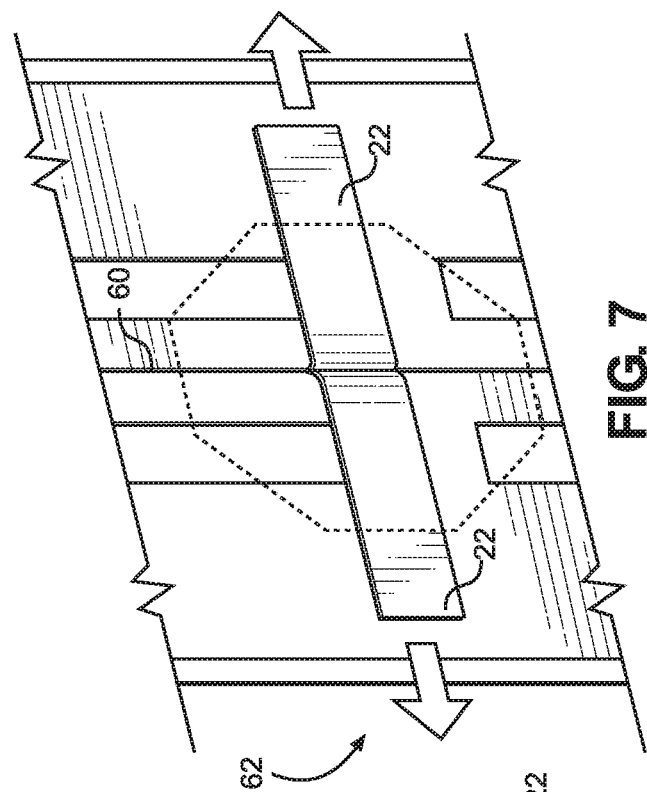
FIG. 7 is a diagrammatic view of an exemplary embodiment of the final step in applying the present safety device 100 invention first door seal.
Figure 6:
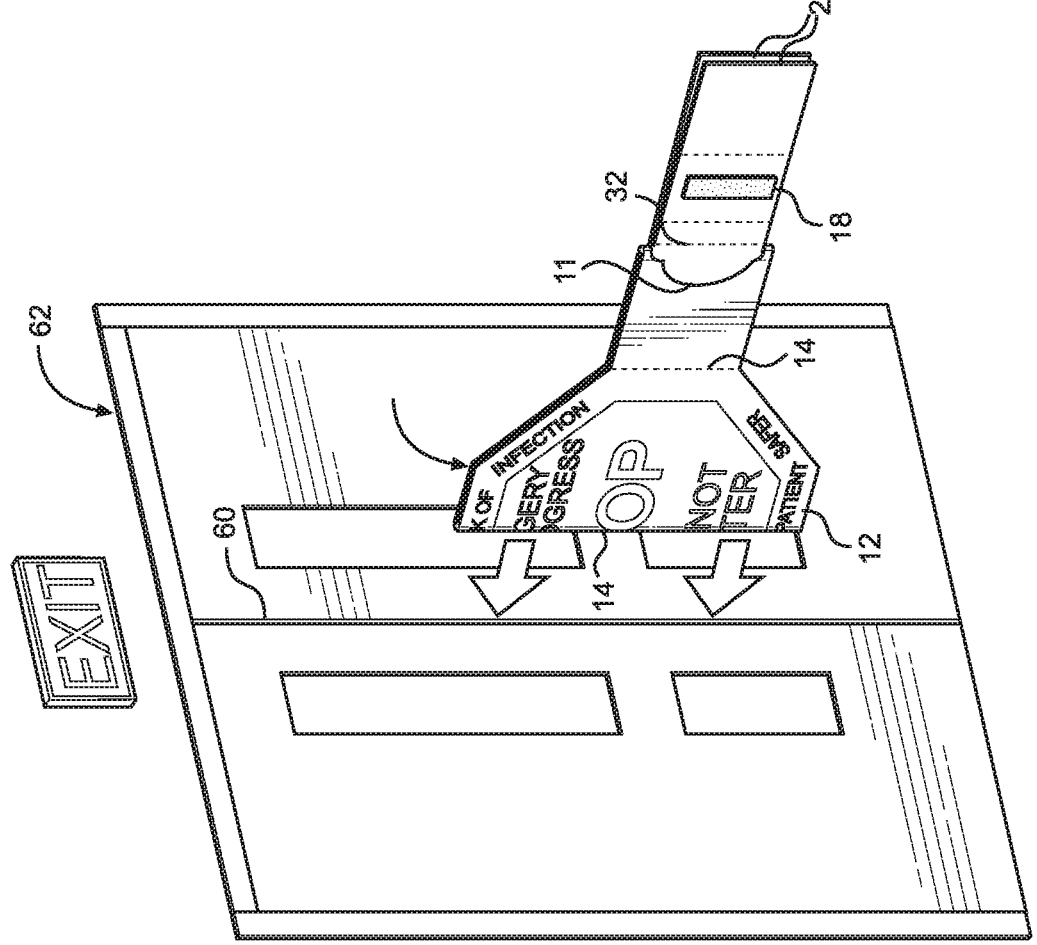
FIG. 6 is a diagrammatic view of an exemplary embodiment of a first step in applying the present safety device 100 invention.

Along the front surface is warning indicia 42, such as text, displays or the like that conveys a warning message, which may vary depending on the perioperative setting or theatre. The warning indicia 42 is provided along a front surface a warning structure 12. The warning structure 12 may be two portions, separable in a flat condition, that engage each other in the operable condition, as illustrated in FIG. 5. Each portion of the warning structure 12 may be disposed on opposing sides of the center of the first perioperative safety device 100, as illustrated in FIG. 1. Each portion of the warning structure 12 may provide a distal flange 15 that mate the other distal flange 5 in said operable condition.

The tabs 22 may provide a removably connector 18, such as strips of double-sided adhesives or the like, enabling temporarily attachment the first perioperative safety device 100 in the operative condition to an exterior/outward facing of the main doors 62 so that the warning indicia 42 is visible along the exterior of the main doors 62.

A perforated edge 32 may be provided between the tab 22 and an associated warning structure 12 portion, wherein the perforated edges allows easy dismantling if the main door seal is broken. The perforated edge 32 demonstrates where the structure would tear or dismantle in the event a necessary intrusion would be needed. The event(s) such as bringing in a code cart, a C-arm to take an X-ray or other life-saving equipment/tools are examples. Once the main door seal/sign is torn/broken, a new main door sign would b installed and documented in the medical record.

The first perioperative safety device 100 is for the main door 62. The first perioperative safety device 100 may be inserted in the slidable condition through the gap 60 thereof, and then folded to the operable condition and by pulling tabs 22 simultaneously (see FIG. 7). The tabs 22 have removable connectors 18 for securing the first perioperative safety device 100.

Referring now to FIGS. 8 and 9, the perioperative safety system of the present invention provides a second perioperative safety device 200 adapted to adhere to exterior of the sub sterile door 64. The second perioperative safety device 200 may include an outward-facing warning indicium 42 and an opposing rear surface 40 having removable connectors 18 for attaching the second perioperative safety device 200 to the exterior of the sub sterile door 64.

Referring now to FIGS. 10 through 14, the perioperative safety system of the present invention provides a third perioperative safety device 300 adapted to provide a multi-detachable band barrier for monitoring intrusions into the perioperative surgical suite. The third perioperative safety device 300 may provide two connection points 54, one connection point mounted on and along an interior the doorway or one the door jam of either the main door 62 or the sub sterile door 64, and the other connection point mounted on adjacent wall, being careful not to occlude door hardware.

The third perioperative safety device 300 may secured with male/female removable connectors 30 at opposing ends thereof. In embodiments, one removable connector 30 at the distal end of a band 46, and another removable connector 30 along a periphery of the warning structure 16 of the warning indicium 42. Each opposing end of the third perioperative safety device 300 attaches to one of the two connection points 54, wherein the band 46 stretches across an interior of each doorway (the main doors 62 or the sub sterile door 64) so that each time either door is opened the band barrier 46 physically detaches from the associated receptacle receiver 54. The removably connectors 30 on the distal end of the band 46 may be a hook and loop fasteners ½" in diameter allowing for detachment when door opens, while the removable connector 30 on the warning structure 16 may be at least twice the surface area—e.g., 1"×1"—preventing it from detaching prior to the other removable connector detaching.

In embodiments, a 8"-10" band barrier, mini 3½"×3½" warning sign, hook and loop male/female attachments (clips on mini warning signage ½"×½", and opposing clip 1"×1".

In some embodiments, the present invention may include the following: 4"×4" receptacle receivers, a plurality of paper forms/monitoring/recording documentation tools; and a plastic bag dimensioned and adapted to store the perioperative safety devices 100, 200 and 300 and/or other systemic components of the present invention.

Furthermore monitoring/documentation tools are associated with the perioperative safety system for documenting entries. When done, the case signage and documentation tools are placed in the original plastic bag and given to designated personnel.

In short, the first perioperative safety device 100 is attached to the outside of the main door 62 for alerting personnel to not enter therethrough. The second perioperative safety device 200 may be attached to the outside of the sub sterile door 64. Verbiage provided along the warning indicia 42 alerts personnel to patient safety reminders. When personnel enter through this door, the third perioperative safety device 300 breaks away and entry is documented via the monitoring/documentation tool. The first perioperative safety device 100 sign keeps personnel out (but can be broken in case of emergency).

Figure 15:
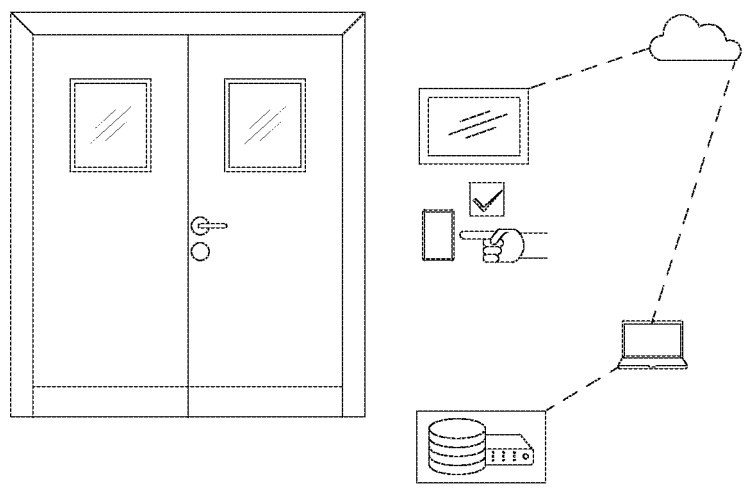
FIG. 15 is a schematic view of an exemplary embodiment of a touchscreen entry associated with the main doors of the present invention.

Referring to FIG. 15, the present invention may include a monitoring device embodied in a touchscreen entry mounted outside of the operating room door 62. Prior to an employee, vendor, sales representative, etc. entering the operating room through the main door, he/she must manually log in by utilizing the touchscreen monitor. All employees, vendor, sales representative, etc. will have been provided a personal code for entry. This touchscreen will match the personal code and document the name of the employee, their credentials, the time of entry and any other information the facility deems necessary for monitoring entries into the operating room. Once the employee, vendor, sales representative, etc. logs in using the touchscreen monitor, this entry will upload into the cloud or via USB cables and interface with the database to document the employee information. This information will be linked to the patient who is in the operating room under a surgical procedure, thus becoming part of the patient's medical record. The employee knows prior to entering the operating room that his/her entry is being tracked, thus enforcing the knowledge that he/she will be accountable for unnecessary intrusions into the operating room during a surgical procedure and that the entry will become part of the patient's medical record.

Figure 16:
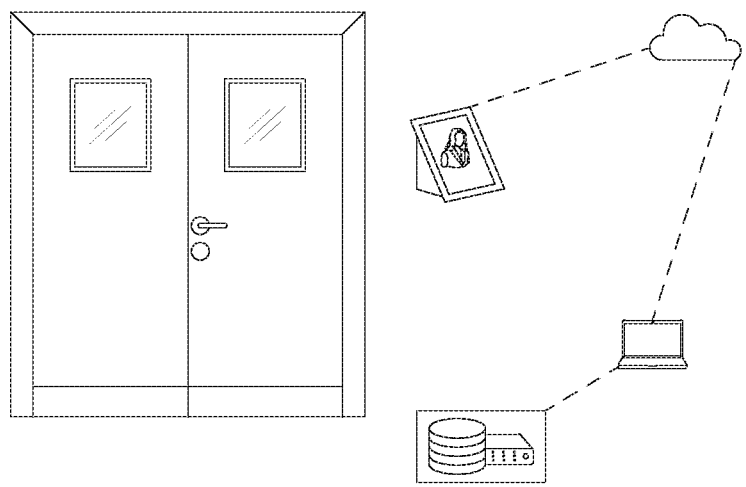
FIG. 16 is a schematic view of an exemplary embodiment of a facial recognition associated with the main doors of the present invention.

Referring to FIG. 16, the present invention may include a monitor with facial recognition technology is mounted outside of the operating room door. Prior to an employee, vendor, sales representative, etc. entering the operating room through the main door, he/she must stand in front of the monitor which will scan and map the facial features and compare the information with known faces to find a match. All employees, vendor, sales representative, etc. will have registered their facial features for the database. Once a match has been found, the facial match is confirmed and the individual's name, credentials, the time of entry and any other information the facility deems necessary for monitoring entries into the operating room is uploaded into the cloud or via USB cables and interfaced with the database. This information will be linked to the patient who is in the operating room under a surgical procedure, thus becoming part of the patient's medical record.

Figure 17:
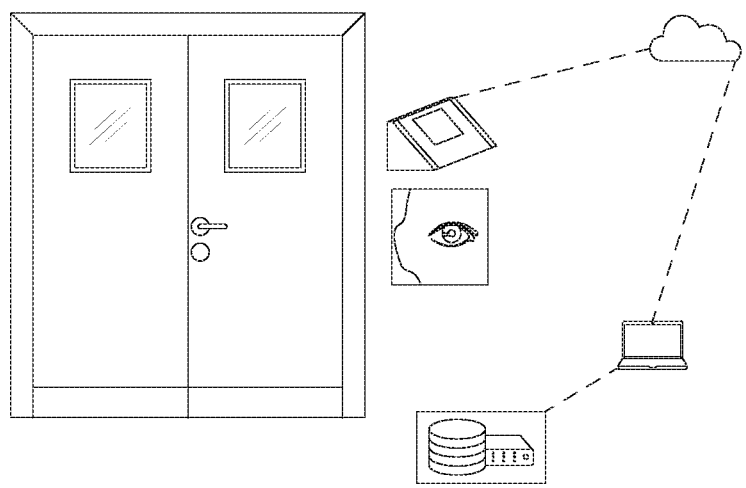
FIG. 17 is a schematic view of an exemplary embodiment of an eye scan associated with the main doors of the present invention.

Referring to FIG. 17, the present invention may include a monitor with eye-scan technology is mounted outside of the operating room door. Prior to an employee, vendor, sales representative, etc. entering the operating room through the main door, he/she must stand in front of the monitor which will perform an iris scan, compare and map the results with known iris scans to find a match. All employees, vendor, sales representative, etc. will have performed an initial eye-scan to register their iris mapping for the database. Once a match has been found, the iris scan match is confirmed and the individual's name, credentials, the time of entry and any other information the facility deems necessary for monitoring entries into the operating room is uploaded into the cloud or via USB cables and interfaced with the database. This information will be linked to the patient who is in the operating room under a surgical procedure, thus becoming part of the patient's medical record.

Figure 18:
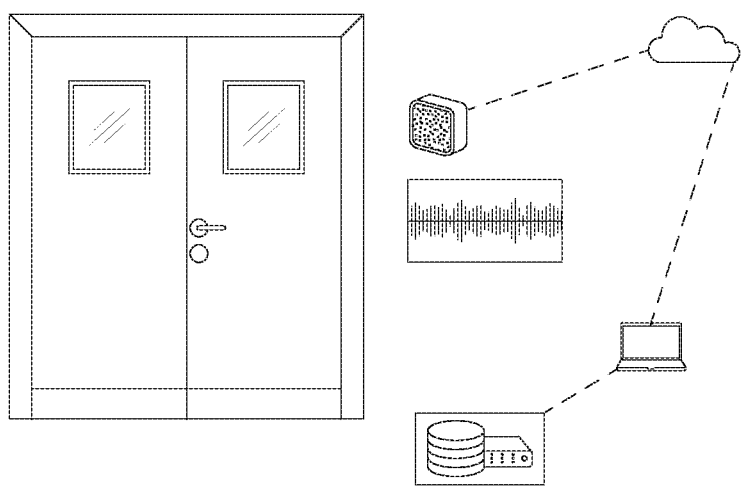
FIG. 18 is a schematic view of an exemplary embodiment of a voice activated entry associated with the main doors of the present invention.

Referring to FIG. 18, the present invention may include a speaker with voice biometric technology is mounted outside of the operating room door. Prior to an employee, vendor, sales representative, etc. entering the operating room through the main door, he/she must stand in front of the speaker and voice a predetermined vocal segment which will perform a voice print search, compare and match the voiceprint identity to the employee. All employees, vendor, sales representative, etc. will have had their unique voice print recorded and tones digitized to create their analog waves into a digital data print within the system. Once the voice authentication is complete and confirmed, the match is used to upload the employee, vendor, sales representative, name, credentials, the time of entry and any other information the facility deems necessary for monitoring entries into the operating room. The voice authentication is uploaded into the cloud or via USB cables and interfaced with the database. This information will be linked to the patient who is in the operating room under a surgical procedure, thus becoming part of the patient's medical record.

Figure 19:
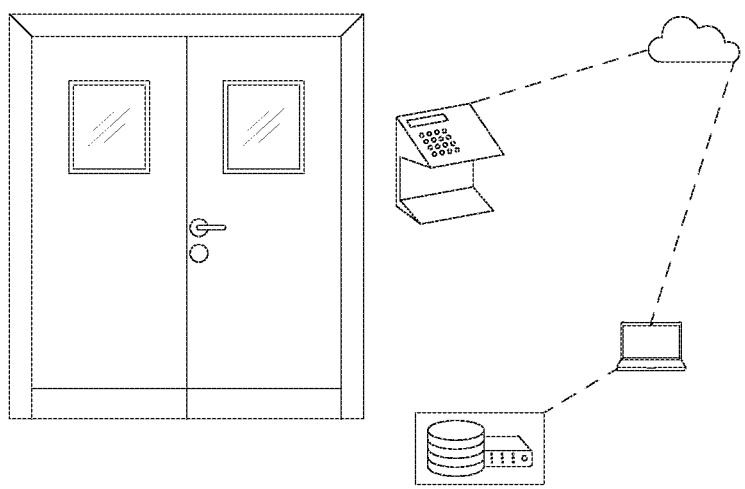
FIG. 19 is a schematic view of an exemplary embodiment of a palm-print activated associated with the main doors of the present invention.

Referring to FIG. 19, the present invention may include a palm print scanner is mounted outside of the operating room door. Prior to an employee, vendor, sales representative, etc. entering the operating room through the main door 62, he/she must place their pre-registered hand-print onto the screen. All employees, vendor, sales representative, etc. will have had their palm pre-registered. When the employee, vendor, sales representative, etc. places his/her hand on the scanner, the database will compare and match the print with the employee and will document the name of the employee, their credentials, the time of entry and any other information the facility deems necessary for monitoring entries into the operating room. Once the individual has their palm scanned, the entry will upload into the cloud or via USB cables and interface with the database to document the employee information. This information will be linked to the patient who is in the operating room under a surgical procedure, thus becoming part of the patient's medical record. The employee, vendor, sales representative, etc. knows prior to entering the operating room that his/her entry is being tracked, thus enforcing the knowledge that he/she will be accountable for unnecessary intrusions into the operating room during a surgical procedure and that the entry will become part of the patient's medical record.

Figure 20:
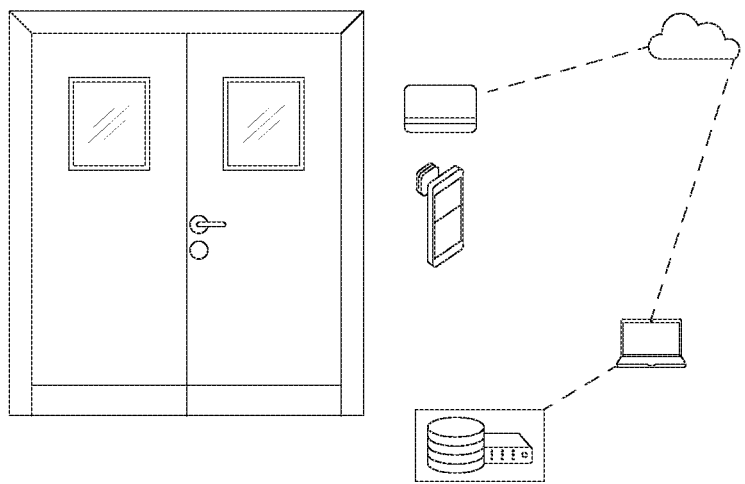
FIG. 20 is a schematic view of an exemplary embodiment of a contactless and chip reader phone entry associated with the main doors of the present invention.

Referring to FIG. 20, the present invention may include a contactless chip reader is mounted outside of the operating room door. Prior to an employee, vendor, sales representative, etc. entering the operating room through the main door, he/she must wave their personal chip card or phone in front of the reader. All employees, vendor, sales representative, etc. will have a chip card or phone with a registered chip or magstripe issued to them. When the individual waves the chip card or phone in front of the scanner, the database will compare and match the reading with the individual's issued card or phone and will document the name of the individual and their credentials, the time of entry and any other information the facility deems necessary for monitoring entries into the operating room. Once the individual or phone is matched within the database, the entry will upload into the cloud or via USB cables and interface with the database to document the employee information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 21:
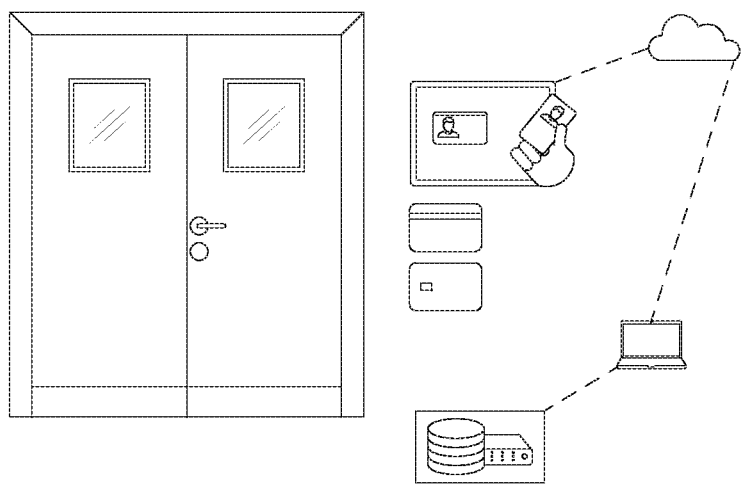
FIG. 21 is a schematic view of an exemplary embodiment of a badge barcode strip or chip reader entry associated with the main doors of the present invention.

Referring to FIG. 21, the present invention may include a barcode stripe and chip reader mounted outside of the operating room door 62. Prior to an employee, vendor, sales representative, etc. entering the operating room through the main door must swipe their badge containing a barcode stripe or enter their employee, vendor, sales representative, etc. badge with the chip inserted into the reader. All employees, vendor, sales representative, etc. will have been issued a personal employee badge for entry utilization. Individual badges will be registered and issued to each employee, vendor, sales representative, etc. Upon swiping or inserting badge into reader, the data match will be uploaded to document the name of the individual, their credentials, the time of entry and any other information the facility deems necessary for monitoring entries into the operating room. This entry will upload into the cloud or via USB cables and interface with the database to document the individual's information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 22:
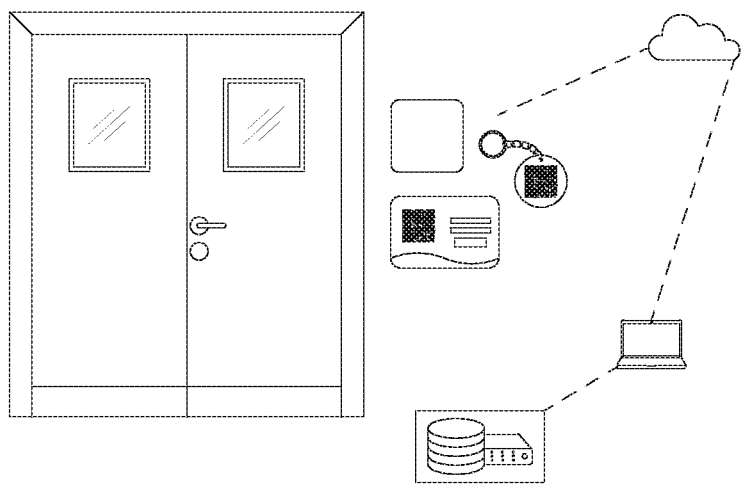
FIG. 22 is a schematic view of an exemplary embodiment of a QR-code activated associated with the main doors of the present invention.

Referring to FIG. 22, the present invention may include a QR scanner mounted outside of the operating room door. Prior to an employee, vendor, sales representative, etc. entering the operating room through the main door, he/she must swipe their employee assigned QR code image in front of the scanner. All employees, vendor, sales representative, etc. will have been issued a personal employee QR code image. The QR code can be located on a badge, a flat surface, an electronic device, a phone, a photo or other surface. Individual QR codes will be assigned to each employee, vendor, sales representative, etc. Upon scanning the QR code into the reader, the data will be matched to the employee, vendor, sales representative, etc. and will be uploaded to document the name of the individual, their credentials, the time of entry and any other information the facility deems necessary for monitoring entries into the operating room. Once the individual scans their QR code, this entry will upload into the cloud or via USB cables and interface with the database to document the employee information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 23:
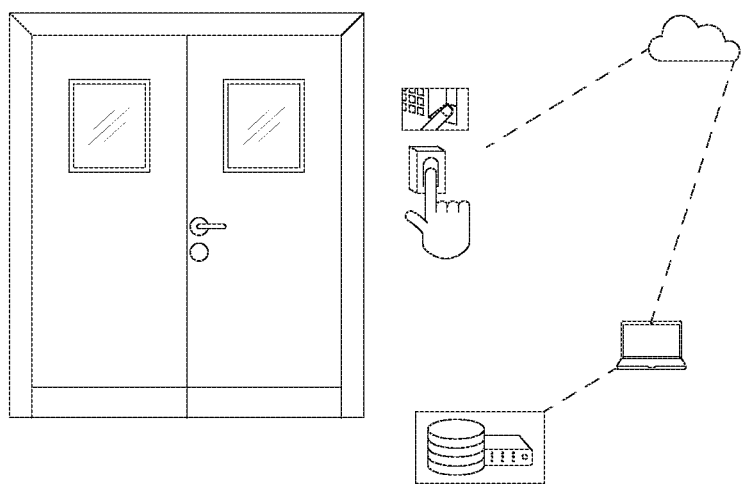
FIG. 23 is a schematic view of an exemplary embodiment of a fingerprint activated entry associated with the main doors of the present invention.

Referring to FIG. 23, the present invention may include a finger-print scanner mounted outside of the operating room door. Prior to an employee, vendor, sales representative, etc. entering the operating room through the main door, he/she must place their pre-registered finger onto the screen. All employees, vendor, sales representative, etc. will have had their fingers scanned and prints registered within the database. The scanner will match the fingerprint to the employees, vendor, sales representative, etc. registered print and will document the name of the individual, their credentials, the time of entry and any other information the facility deems necessary for monitoring entries into the operating room. Once the individual has his/her finger scanned, the entry will upload into the cloud or via USB cables and interface with the database to document the employee information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 24:
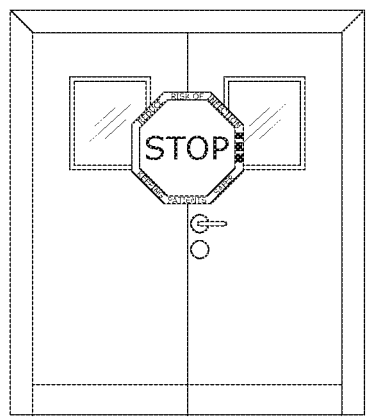
FIG. 24 is a schematic view of an exemplary embodiment along an exterior of the main doors of the present invention.

Referring to FIG. 24, the present invention may include a warning indicium, possibly embodied in a second or third perioperative safety device 200 or 300, and sometimes called "S.I.P.S.—Surgery In Progress . . . STOP!" The second or third perioperative safety device 200 or 300 may be deployed from within the operating room to the outside door. The sign serves as a barrier for employees, vendor, sales representative, etc. who may want to unnecessarily enter the operating room suite. Unlike devices/monitors that are affixed to walls or located on desktops and tables outside or inside the operating room suite, this barrier must be broken in order to enter the operating suite once the sign has been deployed. The main door of the O.R. suite should stay closed at all times during a surgical procedure in order to maintain a constant laminar flow. Once the laminar flow has been disrupted by the door opening, airborne contaminates can fall into the surgical incision and onto the sterile field. The second or third perioperative safety device 200 or 300 may be perforated and can easily be broken if an intrusion is absolutely necessary such as in the event of an X-ray, Code Blue event, etc. To break the sign, simply open the door and the perforation will tear, breaking the barrier. A new sign will need to be used each time the barrier is broken. The display of the sign will also serve as a visual deterrent for unnecessary intrusions into the operating room which will disrupt the laminar flow and expose the patient to airborne contaminates, thus increasing the risk for infection. The goal is to limit traffic within the sterile setting by implementing assessment and monitoring processes to protect the patient by limiting exposure from unnecessary airborne contaminates. The sign is an indication that extra infection control practices are being practiced by the facility. By having a barrier that must be physically broken to enter the surgical suite, it places more awareness, accountability and responsibility on the employee, vendor, sales representative, etc. for their actions.

Figure 25:
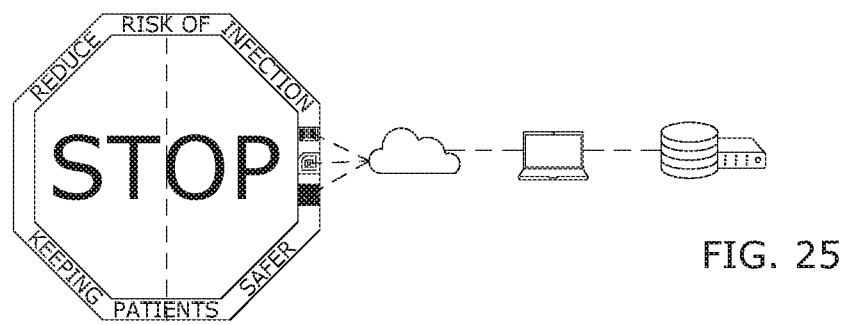
FIG. 25 is a schematic view of an exemplary embodiment of the present invention, demonstrating a sign with a barcode/RFID/QR-code to scan which may be uploaded into a patient medical records.

Referring to FIG. 25, the present invention may include a sign embodying a warning indicium 42, as described in FIG. 24, serves as a barrier that must be physically broken to enter the surgical suite. The sign will have a barcode/QR code/RFID chip displayed that must be scanned when opened prior to deployment. This will link and associate the patient to the barrier used. Once scanned, a verification will be uploaded via the cloud or via USB cables to the patient's medical record in the electronic medical record database.

This verification may also cause a pop-up window to be displayed in the medical record and will generate information, such as the number of intrusions during the surgical procedure and any other information tailored to the facility for reporting purposes. A visual deterrent for the main door 62 entryway which must be physically broken to enter the operating room suite will be less likely to be ignored by personnel, than permanent devices used for scanning or badging in and out are.

Having a unique assessment and monitoring tool method with supporting documentation generated from the initial implementation of the sign's barcode/QR code/RFID chip scan, will provide additional supporting evidence that infection control practices are being enforced.

The sign illustrated in FIG. 25 may stand alone, be affixed to a window or be use with a barrier device.

Figure 26:
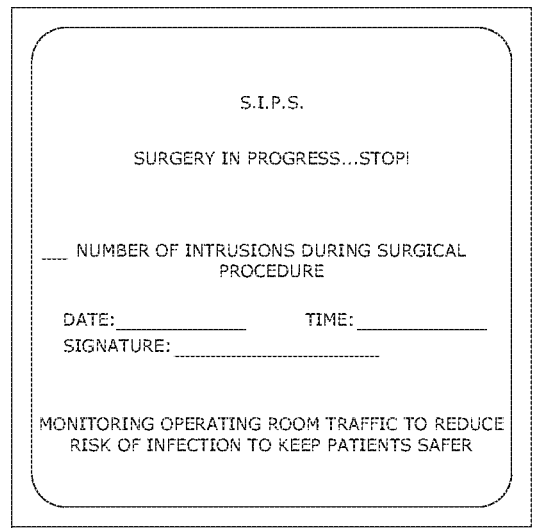

Referring to FIG. 26, the present invention may include a sticker will be accompanied with the sign for use within the patient medical record to indicate monitoring operating room traffic is being performed. This sticker is evidence that the facility is utilizing practices to reduce the risk of infection through monitoring unnecessary intrusions during surgical procedures. For reporting purposes, this sticker is a concrete and valid verification that AORN recommended standards for monitoring and limiting operating room traffic are being practiced. The sticker will be placed on a Progress Report form, Order form, or other form specific to the facility, and will be filled out in its entirety at the end of the surgical procedure.

The sticker may also be referred to as the "S.I.P.S.—Surgery In Progress . . . STOP!" sticker will be scanned into the patient's medical record, and will become part of the patient's permanent medical record. The sticker will be verification when governing bodies and other entities are inspecting infection control practices within a facility. The sticker can also be used to help protect the facility if a patient develops an infection by showing the number of intrusions during a surgical procedure. The hope is that once the facility adopts this practice, there will be a limited amount of intrusions in surgical procedures.

Insurance company claims of infections caused during surgical procedures activities can either be supported or discounted due to the evidence documented on the "S.I.P.S.—Surgery In Progress . . . STOP!" sticker which will reveal AORN recommended practices are implemented and being enforced to limit traffic in the operating room.

Figure 27:
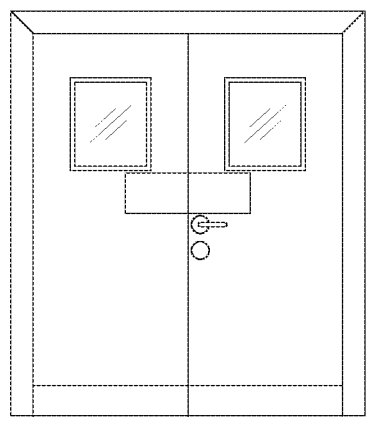
FIG. 27 is an elevation view of an exemplary embodiment of an interior of the main doors of the present invention.

Referring to FIG. 27, the present invention may include a "S.I.P.S. —Surgery In Progress . . . STOP!" sign embodied in a first perioperative safety device 100 deployed, wherein the two tabs 22 which will be adhered to the inside of each main door 62. The low-tack, removable, non-permanent adhesive may be a type of E-Z-release glue and will not leave a residue. The purpose is to provide a temporary mount for supporting the "S.I.P.S.—Surgery In Progress . . . STOP!" sign, and an easy removable, non-permanent fixture on the door surfaces. Once the surgical procedure has been completed, clean-up will be easy by simply removing the adhesive and wiping with an approved disinfectant used on all flat surfaces within the OR. No additional cleaning supplies are needed.

Figure 28:
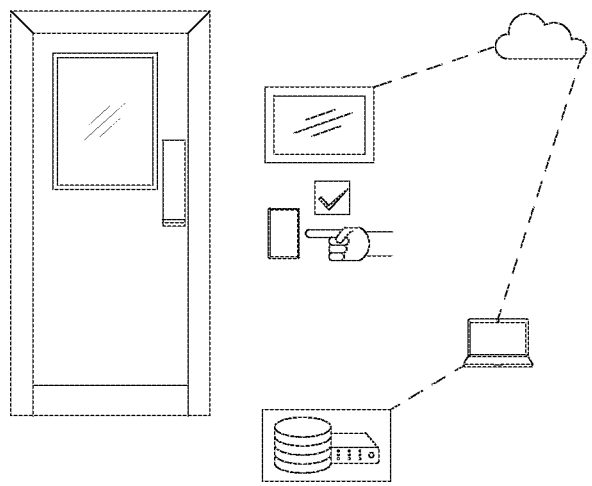
FIG. 28 is a schematic view of an exemplary embodiment of the touchscreen entry associated with the sub sterile door of the present invention.

Referring to FIG. 28, the present invention may include a monitor with touchscreen entry mounted outside of the sub sterile door leading into the operating room. Prior to an employee, vendor, sales representative, etc. entering the operating room through the sub sterile door, he/she must manually log in by utilizing a touchscreen monitor. All employees, vendor, sales representative, etc. will have been provided a personal code for entry. This touchscreen will match the personal code and document the name of the employee, vendor, sales representative, etc. their credentials, the time of entry and any other information the facility deems necessary for monitoring entries into the operating room. Once the individual logs in using the touchscreen monitor, this entry will upload into the cloud or via USB cables and interface with the database to document the individual's information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 29:
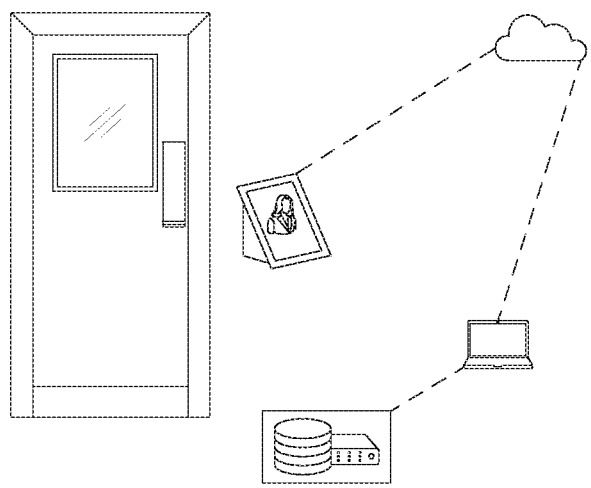
FIG. 29 is a schematic view of an exemplary embodiment of the facial recognition associated with the sub sterile door of the present invention.

Referring to FIG. 29, the present invention may include a monitor with facial recognition technology mounted outside of the sub sterile door 64 leading into the operating room. Prior to an employee, vendor, sales representative, etc. entering the operating room through the sub sterile door, he/she must stand in front of the monitor which will scan and map the facial features and compare the information with known faces to find a match. All employees, vendor, sales representative, etc. will have registered their facial features for the database. Once a match has been found, the facial match is confirmed and the individual's name, credentials, the time of entry and any other information the facility deems necessary for monitoring entries into the operating room is uploaded into the cloud or via USB cables and interfaced with the database. This information will be linked to the patient who is in the operating room under a surgical procedure, thus becoming part of the patient's medical record.

Figure 30:
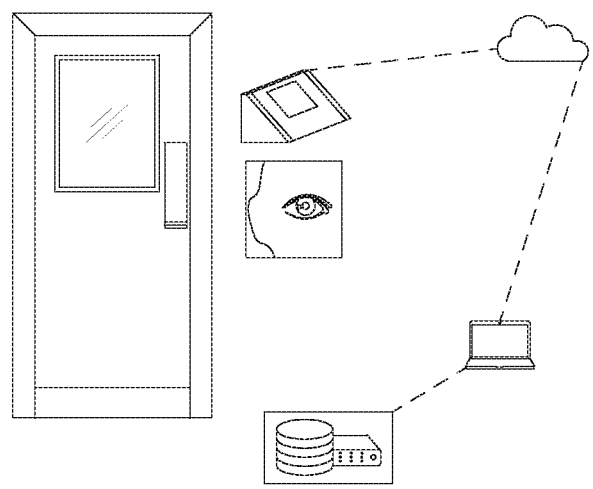
FIG. 30 is a schematic view of an exemplary embodiment of the eye scan associated with the sub sterile door of the present invention.

Referring to FIG. 30, the present invention may include a monitor with eye-scan technology mounted outside of the sub sterile door leading into the operating room. Prior to an employee, vendor, sales representative, etc. entering the operating room through the sub sterile door, he/she must stand in front of the monitor which will perform an iris scan, compare and map the results with known iris scans to find a match. All employees, vendor, sales representative, etc. will have performed an initial eye-scan to register their iris mapping for the database. Once a match has been found, the iris scan match is confirmed and the individual's name, credentials, the time of entry and any other information the facility deems necessary for monitoring entries into the operating room is uploaded into the cloud or via USB cables and interfaced with the database. This information will be linked to the patient who is in the operating room under a surgical procedure, thus becoming part of the patient's medical record.

Figure 31:
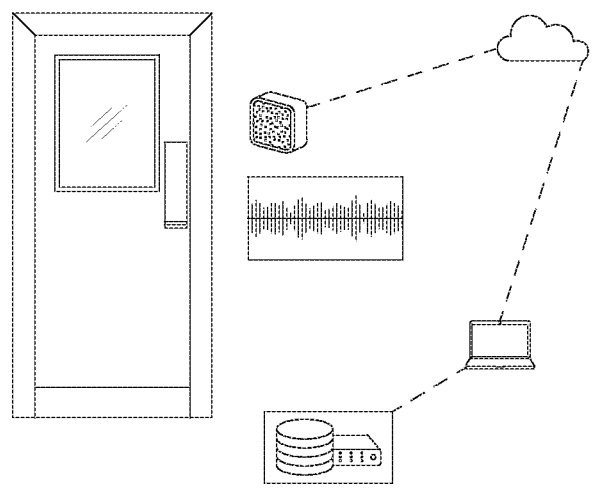
FIG. 31 is a schematic view of an exemplary embodiment of the voice activated entry associated with the sub sterile door of the present invention.

Referring to FIG. 31, the present invention may include a speaker with voice biometric technology mounted outside of the sub sterile door leading into the operating room. Prior to an employee, vendor, sales representative, etc. entering the operating room through the sub sterile door, he/she must stand in front of the speaker and voice a predetermined vocal segment which will perform a voice print search, compare and match the voiceprint identity to the employee, vendor, sales representative, etc. All employees, vendor, sales representative, etc. will have had their unique voice print recorded and tones digitized to create their analog waves into a digital data print within the system. Once the voice authentication is complete and confirmed, the match is used to upload the individual's name, credentials, the time of entry and any other information the facility deems necessary for monitoring entries into the operating room. The voice authentication is uploaded into the cloud or via USB cables and interfaced with the database. This information will be linked to the patient who is in the operating room under a surgical procedure, thus becoming part of the patient's medical record.

Figure 32:
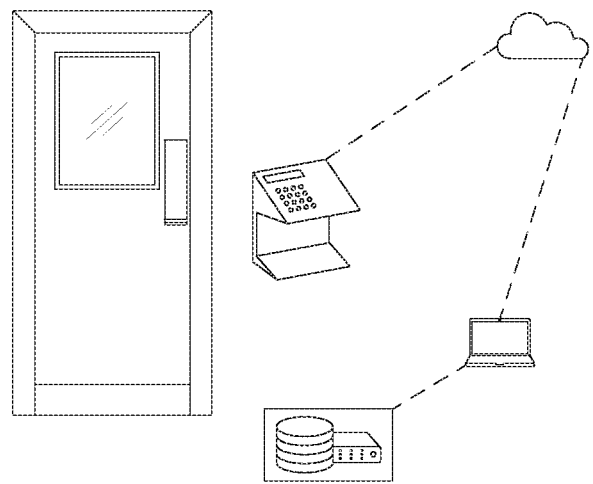
FIG. 32 is a schematic view of an exemplary embodiment of the palm-print activated associated with the sub sterile door of the present invention.

Referring to FIG. 32, the present invention may include Referring to FIG. 15, the present invention may include a palm print scanner mounted outside of the sub sterile door leading into the operating room. Prior to an employee, vendor, sales representative, etc. entering the operating room through the sub sterile door, he/she must place their pre-registered handprint onto the screen. All employees, vendor, sales representative, etc. will have had their palm pre-registered. When the individual places his/her hand on the scanner, the database will compare and match the print with the employee and will document the name of the individual, their credentials, the time of entry and any other information the facility deems necessary for monitoring entries into the operating room. Once the employee, vendor, sales representative, etc. has his/her palm scanned, the entry will upload into the cloud or via USB cables and interface with the database to document the individual's information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 33:
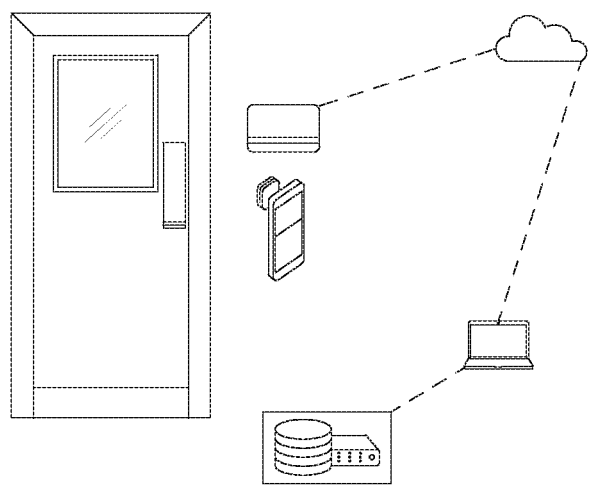
FIG. 33 is a schematic view of an exemplary embodiment of the contactless and chip reader phone entry associated with the sub sterile door of the present invention.

Referring to FIG. 33, the present invention may include a contactless chip reader mounted outside of the sub sterile door leading into the operating room. Prior to an employee, vendor, sales representative, etc. entering the operating room through the sub sterile door, he/she must wave their personal chip card or phone in front of the reader. All employees, vendor, sales representative, etc. will have a chip card or phone with a registered chip or magstripe issued to them. When the individual waves the chip card or phone in front of the reader, the database will compare and match the reading with the employee's issued card or phone and will document the name of the individual and their credentials, the time of entry and any other information the facility deems necessary for monitoring entries into the operating room. Once the individual's card or phone is matched within the database, the entry will upload into the cloud or via USB cables and interface with the database to document the individual's information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 34:
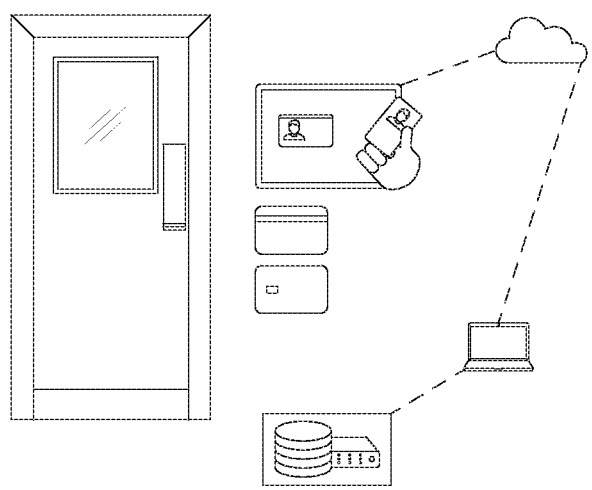
FIG. 34 is a schematic view of an exemplary embodiment of the badge barcode strip or chip reader entry associated with the sub sterile door of the present invention.

Referring to FIG. 34, the present invention may include a barcode stripe and chip reader mounted outside of the sub sterile door leading into the operating room. Prior to an employee, vendor, sales representative, etc. entering the operating room through the sub sterile door, he/she must swipe their individual badge containing a barcode stripe or enter their individual badge with the chip inserted into the reader. All individuals will have been issued a personal employee badge for entry utilization. Individual badges will be registered and issued to each employee, vendor, sales representative, etc. Upon swiping or inserting badge into reader, the data match will be uploaded to document the individual's name, their credentials, the time of entry and any other information the facility deems necessary for monitoring entries into the operating room. Once the individual's badges in, this entry will upload into the cloud or via USB cables and interface with the database to document the employee information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 35:
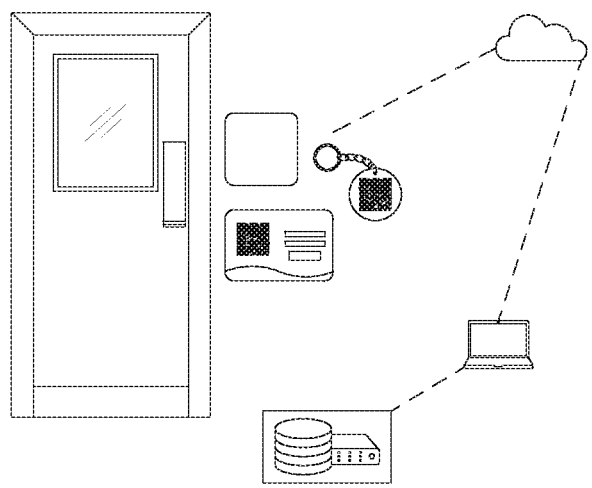
FIG. 35 is a schematic view of an exemplary embodiment of the QR-code activated associated with the sub sterile door of the present invention.

Referring to FIG. 35, the present invention may include a QR scanner mounted outside of the sub sterile door leading into the operating room. Prior to an employee, vendor, sales representative, etc. entering the operating room through the sub sterile door, he/she must swipe their employee assigned QR code image in front of the scanner. All employees, vendor, sales representative, etc. will have been issued a personal employee QR code image. The QR code can be located on a badge, a flat surface, an electronic device, a phone, a photo or other surface. Individual QR codes will be assigned to each employee, vendor, sales representative, etc. Upon scanning the QR code into the reader, the data will be matched to the individual and will be uploaded to document the individual's name their credentials, the time of entry and any other information the facility deems necessary for monitoring entries into the operating room. Once the individual scans their QR code, this entry will upload into the cloud or via USB cables and interface with the database to document the individual's information. This information will be linked to the patient who is in the operating room under a surgical procedure, thus becoming part of the patient's medical record. Thus the individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 36:
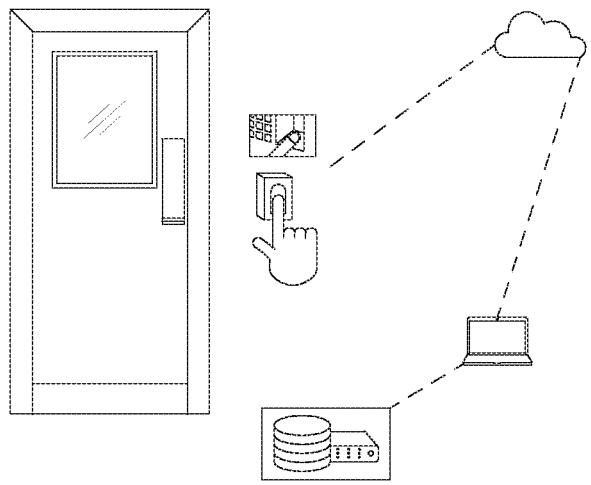
FIG. 36 is a schematic view of an exemplary embodiment of the fingerprint activated entry associated with the sub sterile door of the present invention.

Referring to FIG. 36, the present invention may include a fingerprint scanner mounted outside of the sub sterile door leading into the operating room.

Prior to an employee, vendor, sales representative, etc. entering the operating room through the sub sterile door, he/she must place their pre-registered finger onto the screen. All employees, vendor, sales representative, etc. will have had their fingers scanned and prints registered within the database. The scanner will match the fingerprint to the employee, vendor, sales representative, etc. registered print and will document the individual's name, their credentials, the time of entry and any other information the facility deems necessary for monitoring entries into the operating room. Once the employee, vendor, sales representative, etc. has his/her finger scanned, the entry will upload into the cloud or via USB cables and interface with the database to document the individual's information. This information will be linked to the patient who is in the operating room under a surgical procedure, thus becoming part of the patient's medical record. The individual knows prior to entering the operating room that his/her entry is being tracked, thus enforcing the knowledge that he/she will be accountable for unnecessary intrusions into the operating room during a surgical procedure and that the entry will become part of the patient's medical record.

Figure 37:
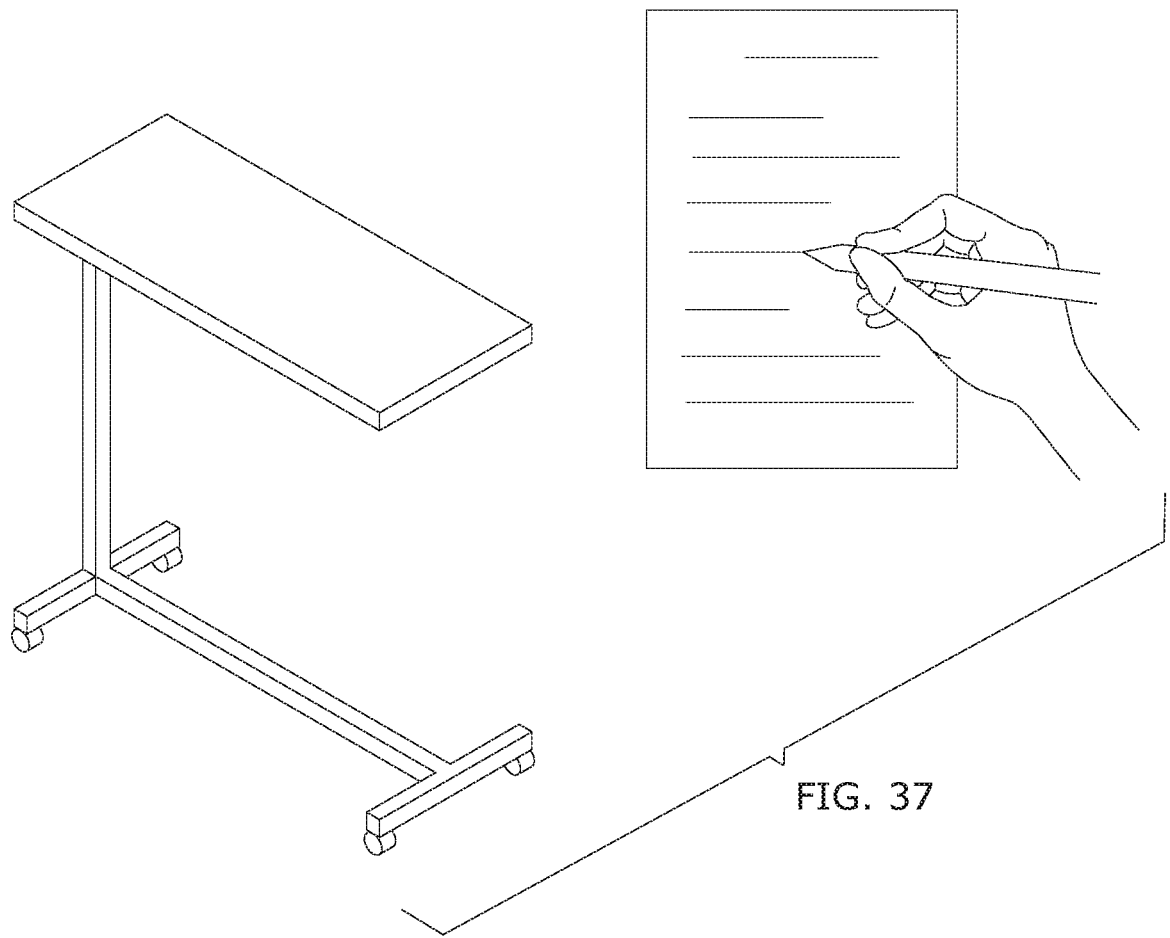
FIG. 37 is a schematic view of an exemplary embodiment of manual handwritten forms of the present invention.

Referring to FIG. 37, the present invention may include a method to facilitate who have not implemented electronic medical records, and so manual handwritten documentation may be required. The use of the "S.I.P.S.—Surgery In Progress . . . STOP!" sticker can be utilized to document the number of intrusions and will have the date, time and verifier's signature attached to provide a recording of the AORN recommendation for limiting operating room traffic. Additional documentation tailored to the facility can be utilized to assess, monitor and report unnecessary intrusions into the operating room while surgical procedures are underway. Quality improvement studies can be generated from the documentation tools and used to improve practices.

Figure 38:
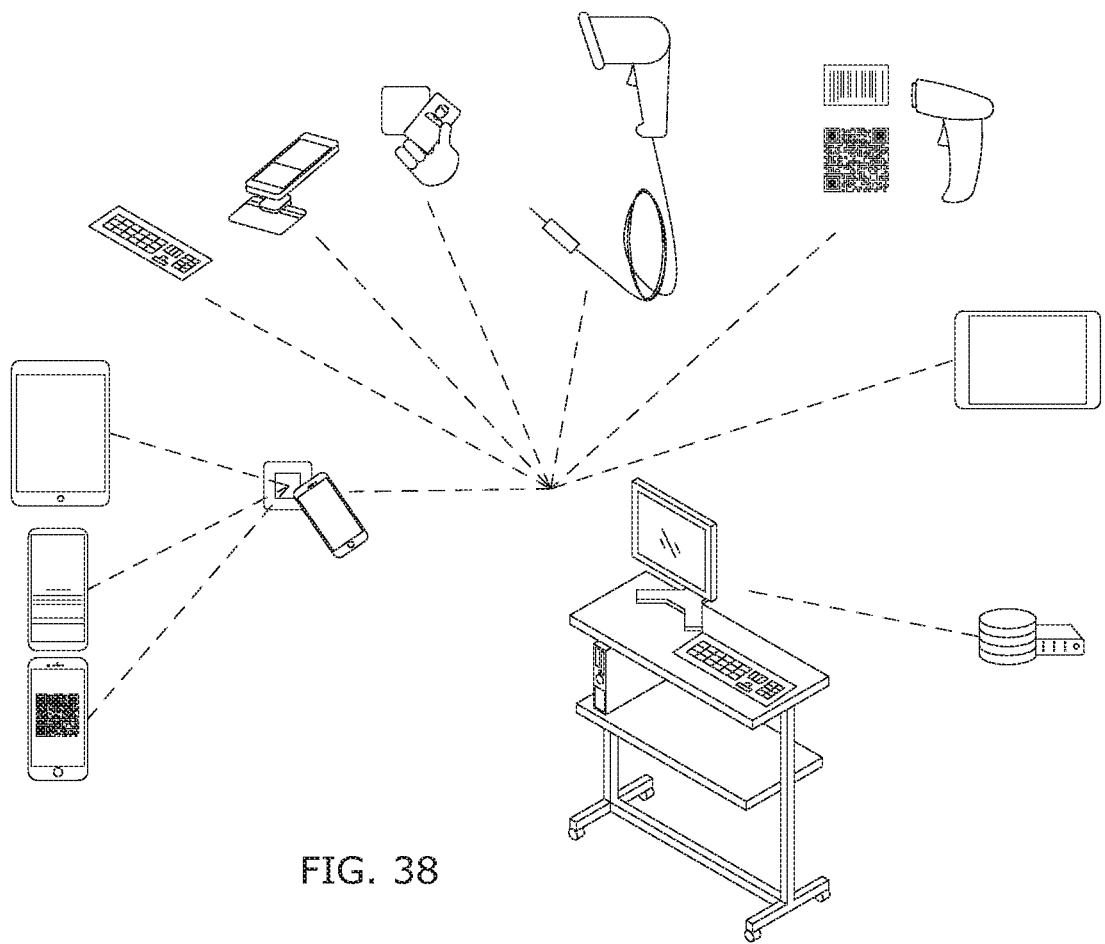
FIG. 38 is a schematic view of an exemplary embodiment of the present invention, demonstrating an operating room main control hub.

Referring to FIG. 38, the present invention may incorporate the nurse's workstation or table near the sub sterile door entrance, and related devices for scanning will be located. These devices may include contactless chip and scanning platforms, chip readers, RFID readers, QR code scanners, barcode scanners, keyboards for computer entry, I-pods or tablets for computer entry, I-phones and other devices for facial recognition, fingerprint recognition, etc. and will be utilized to document each intrusion into the operating room. Each employee, vendor, sales representative, etc. will be required to provide the appropriate methodologies of scanning practices to register each intrusion into the operating room suite.

This information may be uploaded via cloud, cables, or the like for interfacing with the database to document the entrant's information. This information will be linked to the patient who is in the operating room under a surgical procedure, thus becoming part of the patient's medical record. Thus, the entrant knows prior to entering the operating room that his/her entry is being tracked, thus enforcing the knowledge that he/she will be accountable for unnecessary intrusions into the operating room during a surgical procedure and that the entry will become part of the patient's medical record.

Figure 39:
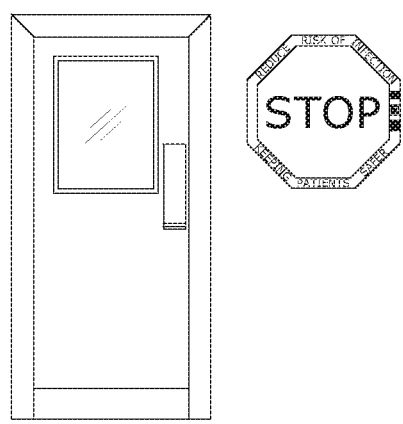
FIG. 39 is an elevation view of an exemplary embodiment of an interior of the sub sterile door of the present invention.

Referring to FIG. 39, the present invention may include a second or third perioperative safety device 200 or 300; for instance a miniature "S.I.P.S.—Surgery In Progress . . . STOP!" sign with a bright colored stretchable banner that affixes temporarily to the door and stretches to a wall plate. This serves as a barrier for entrants who are wanting to enter the operating room via the sub sterile doorway access. Each end piece has a tab which is temporarily affixed to the door with one end attached to the door, the other end stretched across the door jam to the wall. One tab will have more of a low-tack, removable, non-permanent adhesive such as an E-Z-release glue which will not leave a residue when removed. The other tab will have half or less of the amount so that when the door is opened, it will easily detach from the surface, leaving the other tab in place. When the door is opened, one end piece will dislodge and dangle until it is reattached to either the door or wall, recreating the barrier across the doorway. The bright color serves to remind the entrant that they are being monitored, thus enforcing the need to limit traffic in and out of the operating room during the surgical procedure. Since access via the sub sterile door will be utilized during a surgical procedure, the device is used for multiple-use during the procedure, but for single use only for each case. Although used inside the operating room suite, it reminds and brings awareness to entrants that they need to limit their entries. The visual deterrent will reduce the disruption of laminar flow by bringing awareness that all door openings are being documented and entrant's names, credentials, number of times entering and existing the room, will be documented and will become part of the patient's medical record. The goal is to limit traffic within the sterile setting by implementing assessment and monitoring processes to protect the patient by limiting exposure from unnecessary airborne contaminates. The second and third perioperative safety devices 200 and 300 are an indication that extra infection control practices are being practiced and by having a barrier, it places more awareness, accountability and responsibility on the entrant for their actions. Each time the barrier is interrupted, a designated person, usually, the nurse in the room, is responsible for documenting each event either manually, electronically or by utilizing the scanning systems available.

Alternatively, the main door sign, elements to make the present invention work better and more efficiently can include utilizing different colors and/or different sizes and shapes of the signage. Wording of the warning indicium 42 can be a variety of different phrases, fonts can be larger or smaller or even in different font themes. LED lights in a variety of different colors can be added for better visualization. The lights can be displayed in various patterns and/or angles on or near the sign. Intrusion sensors can be added, such as audible noise makers (bells, whistles, buzzers, clickers automated voice broadcasting/notification and/or flashing lights, etc.) which will activate once the sign has been altered when an intrusion occurs. There can also be notifications sent to cell phones, applications, computers and/or other electronic devices when an intrusion occurs.

Different adhesives or glues, securement devices and connections such as hooks, magnets, clips, retractable ties, cords, buttons, flags, banners, reflective and/or plain strings, banners, stretchy or retractable barriers and ribbons can be used. The Alterations can make the signage for single use or for multiple use.

An indicator sticker or other application can be used to affix to the patient's paper medical record for tracking purposes. The indicator can have a variety of wordings, visualization aides, shapes, sizes, colors, barcodes, QR codes for scanning, RDIF scanning codes, digital codes, chips, model numbers, reference numbers, serial numbers and tracking numbers that correlate back to the product that are manually adhered into the chart which can correlate back to the use of the product. When paper charting is not utilized, then each sign may possess an indicator (either directly on the sign or in the signs package material) which can be either a single or a combination of barcodes, RFID's, QR codes, digital security codes, reference numbers, model numbers, item numbers or other tracking numbers and/or letters, and/or chips which can be scannable for uploading information using software, into the patients electronic medical record. Uploads can occur using software for electronic applications and other electronic transmissions which can be used with applications linked to cell phones, computers, tablets, scanners, keyboards and other electronic devices. They may also be manually entered into the electronic medical record utilizing compatible software, apps, Bluetooth transmissions, UBS cords, electrical cords, etc. The indicator is used for tracking and monitoring any intrusion into the surgical suite while surgery is in progress.

For any secondary door or other entrance/exits (also known as sub sterile or Core Doors), the same as listed above for the Main door applies. Plus, since the secondary door will be utilized for multiple intrusions, there are several additional alterations to the design which will make the invention work more effectively for monitoring and tracking who is entering and exiting the surgical suite. Both manual and/or electronic devices can be used either with a single or combination of alerts as listed above. Some operating rooms do not have secondary doors 64, so all items listed above for main doors 62 and their variations may be used. The manual or electronic devices can be positioned outside or inside the secondary door: a keypad entry with individual pin numbers associated with each employee and/or vendor, a voice activated transducer, a badge containing a barcode or Chip, RFID or QR code for scanning, biometrics authentication methods such as fingerprint or palm scanner, fingerprint identification, retinal or iris scanner, facial recognition scanner, facial authentication, face-detection, voice authentication, hand written identification, Square terminal or PED's (Pin Entry Devices) which can be used with keyboards, touch displays, tablets, cell phones, computers and other electronic devices. These electronic devices will be linked to the patient's electronic medical record either through software applications or other transmitters and electronic means to upload the intrusions, and other information associated with who entered and exited directly into the patient's chart. The information may be tailored for each facility.

The transmitted information will track who entered and exited the surgical suite while the surgical procedure was in progress, as well as their title, the number of intrusions and other information and will become a permanent part of the patient's medical record. The reasoning behind the monitoring and tracking is to ensure the least amount of intrusions into the surgical suite while the surgical procedure is in progress will occur, thus exposing the patient to a limited number of disturbances in the laminar airflow and bacteria and airborne contaminates during the surgical procedure. There can also be a variety of construction material ranging from corrugated and non-corrugated cardboard, construction paper, laminated paper materials, wood, fiberglass, composite, vinyl, metal, polycarbon, nonporous materials, porous materials, flammable and nonflammable material, hypoallergenic materials, latex/non-latex materials, plastic, Velcro, rubber, plexiglass, lexan, glass, fire-retardant materials, leather, mylar and any combination of materials. Each device or combination of devices must not hinder an intrusion in the event of an emergency, but simply serve as a breakable barrier and/or monitoring tool.

Additionally, the present invention could be used in any area to limit traffic/unnecessary intrusions.

It should be understood, of course, that the foregoing relates to exemplary embodiments of the invention and that modifications may be made without departing from the spirit and scope of the invention as set forth in the following claims.

What is claimed is:

1. A perioperative safety system for eliminating unnecessary traffic in an operating room setting, comprising:
    main doors for accessing and egressing the operating room setting;
    an outer perioperative safety device disposed adjacent an outer portion of the main doors, wherein accessing the operating room setting through said main doors requires engaging said outer perioperative safety device; and
    an inner perioperative safety device disposed adjacent an inner portion of the main doors, wherein accessing the operating room setting through said main doors requires moving said inner perioperative safety device, wherein the outer perioperative safety device is electrically connected to a computer, wherein the computer is electrically connected to a medical record of a patient undergoing a surgery in the operating room setting, and wherein engaging said outer perioperative safety device during said surgery is saved in the medical record.

2. The perioperative safety system of claim 1, wherein the outer perioperative safety device is a touchscreen entry device.

3. The perioperative safety system of claim 1, wherein the outer perioperative safety device is a facial recognition entry device.

4. The perioperative safety system of claim 1, wherein the outer perioperative safety device is an eye-scan entry device.

5. The perioperative safety system of claim 1, wherein the outer perioperative safety device is a voice biometric entry device.

6. The perioperative safety system of claim 1, wherein the outer perioperative safety device is a palm-print-scan entry device.

7. The perioperative safety system of claim 1, wherein the outer perioperative safety device is a contactless chip reader entry device.

8. The perioperative safety system of claim 1, wherein the outer perioperative safety device is a barcode entry device.

9. The perioperative safety system of claim 1, wherein the outer perioperative safety device is a QR-scan entry device.

10. The perioperative safety system of claim 1, wherein the outer perioperative safety device is a finger-print entry device.

11. The perioperative safety system of claim 1, wherein the outer perioperative safety device is a generally planar body comprising:
    a center portion extending between a first and second warning structures;
    a pull tab extending from the first and second warning structures away from the center portion;
    the generally planar body foldable between an operable condition and a slidable condition dimensioned to slid through a gap between the main doors, wherein the operable condition mates the first and second warning structures; and
    a warning indicium provided along the first and second warning structures, wherein the warning indicium is visible when accessing the operating room setting through said main doors.

12. The perioperative safety system of claim 11, wherein the warning indicium comprises verbiage that alerts personnel of the patient.

13. The perioperative safety system of claim 11, wherein the planar body comprising a plurality of fold lines for so that the planar body is foldable.

14. The perioperative safety system of claim 11, wherein the first and second warning structures each provide a flange that mates with the other flange in the operable condition.

15. The perioperative safety system of claim 11, wherein the planar body comprises a centrally disposed pull tab opening, and wherein the two pull tabs extend through the pull tab opening when folding from the slidably condition to the operable condition.

16. The perioperative safety system of claim 15, wherein the pull tab opening comprises two diametrically opposing pulse-shaped voids extending upward and downward, respectively, wherein a spaced between the distal tips of each pulse-shaped voids is dimensioned so that the two pull tabs extend therethrough.

17. The perioperative safety system of claim 11, wherein the two pull tabs are disposed along the inner portion of the main doors, and wherein the first and second warning structures are disposed along the outer portion of the main doors in the operable condition.

18. The perioperative safety system of claim 11, wherein the inner perioperative safety device comprising:
    two connection points;
    a sign with a warning indicia; and
    a band, wherein the sign and each band removably attaches to one of the two connection points, respectively, so that the band extends across the gap of the main doors.

19. The perioperative safety system of claim 18, wherein the one of the two connection points associated with the sign is at least twice as connected to the sign as the other of the two connection points is connected to the band.

\* \* \* \* \*